United States Patent [19]

Bell

[11] Patent Number: 5,426,121
[45] Date of Patent: Jun. 20, 1995

[54] WOOD PRESERVATION FORMULATION COMPRISING COMPLEX OF A COPPER CATION AND ALKOXYLATED DIAMINE

[75] Inventor: John P. Bell, Ossining, N.Y.

[73] Assignee: Akzo Nobel N.V., Arnhem, Netherlands

[21] Appl. No.: 319,145

[22] Filed: Oct. 4, 1994

[51] Int. Cl.$^6$ .................. A61K 31/30; C09K 3/18
[52] U.S. Cl. ........................ 514/500; 106/15.05; 106/18.32; 504/121; 504/148; 514/499
[58] Field of Search ............... 514/668, 499, 500; 504/121, 148; 106/15.05, 18.32

[56] References Cited

U.S. PATENT DOCUMENTS

| | | | |
|---|---|---|---|
| 2,734,028 | 2/1956 | Domogalla | 210/23 |
| 4,761,179 | 8/1988 | Goettsche et al. | 106/18.32 |
| 4,857,322 | 8/1989 | Goettsche et al. | 424/633 |
| 4,929,454 | 5/1990 | Findlay et al. | 424/638 |
| 5,186,947 | 2/1993 | Goettsche et al. | 424/638 |
| 5,276,029 | 1/1994 | Goettsche et al. | 514/231.2 |

FOREIGN PATENT DOCUMENTS

| | | | |
|---|---|---|---|
| 238413 | 9/1987 | European Pat. Off. | B27R 3/52 |
| 91/11306 | 8/1991 | WIPO | B27K 3/32 |

OTHER PUBLICATIONS

Chemical Abstracts, vol. 66, 114909w (1967).
New Zealand Journal of Forestry Science, vol. 13, No. 3, pp. 354–363 (1983).
New Zealand Journal of Forestry Science, vol. 9, No. 3, pp. 348–358 (1979).

*Primary Examiner*—Peter O'Sullivan
*Attorney, Agent, or Firm*—Richard P. Fennelly; Louis A. Morris

[57] ABSTRACT

Liquid wood preservation formulations comprise a liquid solvent and a complex dissolved therein which is formed by the reaction of a compound containing a copper cation and an alkoxylated diamine, preferably containing at least one fatty alkyl group, such as an alkoxylated diamine wherein the alkoxylation is either ethoxylation or propoxylation.

13 Claims, No Drawings

WOOD PRESERVATION FORMULATION COMPRISING COMPLEX OF A COPPER CATION AND ALKOXYLATED DIAMINE

BACKGROUND OF THE INVENTION

A variety of wood preservation formulations exist including those which contain a biocidal cation, such as copper, and another compound, including an ammonium compound.

J. A. Butcher et al., in New Zealand Journal of Forestry Science, Vol. 9, pp. 348–358 (1979) describe various unmodified and copper-modified alkylammonium compounds as wood preservatives. The copper-modified species included benzalkonium chloride:cupric chloride, octyldecyldimethyl ammonium chloride:cupric chloride, and cocodimethylamine acetate:cupric acetate.

J. A. Drysdale in New Zealand Journal of Forestry Science 13(3), pp. 354–363 (1983) revealed that copper and dimethylalkylamine salts showed some initial improvement over an amine salt alone. However, in most cases, soluble copper salts, which are often acidic, are too corrosive to add to wood treatment mixtures.

U.S. Pat. No. 4,929,454 of D. M. Findlay et al. describes a system which comprises an aqueous ammoniacal solution of copper and a quaternary ammonium compound which contains an anion to solubilize the quaternary ammonium compound. Such anions as hydroxide, chloride (which is preferred), bromide, nitrate, bisulfate, acetate, bicarbonate and carbonate, formate, borate and fatty acid salts are enumerated. Copper is fixed (i.e. fastened) in the treated wood by decomposition of the tetraamine copper (II) complex that forms during preparation of the ammoniacal copper treating solution.

Wood preservation formulations comprising a biocidal cation, such as one comprising copper, and a polyamine, such as a diamine, are described in U.S. Pat. Nos. 4,761,179, 4,857,322 and 5,276,029 to R. Goettsche et al. In U.S. Pat. No. 5,276,029 certain formulations are used which comprise copper carbonate and ethoxylated coconut fatty amine.

An ammoniacal copper-quaternary ammonium compound formulation was reported to prevent decay by *P. placenta* at 4 kg/m³ of ACQ (2.1 kg/m³ copper oxide). See K. J. Archer et al., "A Proposal to AWPA Committee P4 to Include Ammoniacal Copper Quat, ACQ Type B in AWPA Standards", American Wood Preservers' Association Treatments Committee P4, American Wood Preservers' Association Proceedings, 1990.

SUMMARY OF THE INVENTION

The present invention relates to a wood preservation formulation which comprises a complex of a copper cation and a alkoxylated diamine which shows improved performance over copper-amine complexes.

DETAILED DESCRIPTION OF THE INVENTION

The liquid wood preservation formulation formed by the present invention will comprise water, as the solvent component of the formulation, with the remainder comprising the active wood preservation reagents to be described below along with any other optional additives deemed needed.

The biocidal cation used in the wood preservation formulation of the present invention is derived from a copper reagent that can be either water-soluble or water insoluble.

Representative salts of the copper cation which may be used include the chloride, sulfate, hydroxide, nitrate, formate, acetate, carbonate or bicarbonate, borate or oxide. However, copper compounds that are basic in nature are preferred to those that are acidic. Since multiple copper sources can be used, all further discussion of copper concentrations in the formulations used in accordance with the invention will be expressed on an oxide basis (namely, copper as CuO).

The alkoxylated diamine component of the formulations of the present invention preferably is of the formula

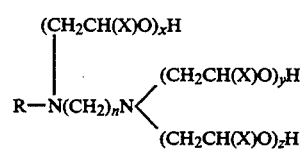

where n is an integer which can vary from 1 to 4, preferably 2 or 3, X is selected from the group consisting of hydrogen, methyl, ethyl, or phenyl, x, y and z are each integers which can be 1 to 6, and R is fatty alkyl of from about 8 to 22 carbon atoms, preferably from 10 to 20 carbon atoms. In the foregoing compounds, X is preferably hydrogen since such compounds form copper complexes that are water soluble at substantially all ratios of copper to diamine.

In the formulations contemplated herein the weight ratio of copper cation (as CuO) to alkoxylated diamine in forming the desired complex will vary from about 1:30 to about 5:1 and the respective weight amounts of each in forming the complex used in the formulation will vary from about below 1% to about 15% and from about 1% to about 60%, respectively. A small coordinating amine, such as ethanolamine or ammoniacal solutions, may be used to fill out the coordination needs of the copper when it is supplied in the form of an insoluble salt.

The formulations of the present invention can contain other ingredients in addition to the foregoing essential reagents used to form the complex between the biocidal cation and alkoxylated diamine. For example, the wood preservation formulation can comprise such other additives as other biocidal compounds or additives, emulsifier(s), pH control agent(s), other solvent(s), such as an alcohol to promote the solubility of the reagents used, and the like.

Two long chain alkoxylated diamines, namely, "Ethoduomeen C/13", more conventionally known as N,N',N'-tris(2-hydroxyethyl)-N-cocoalkyl-1,3-diaminopropane, and "Propoduomeen C/13", more conventionally known as N,N',N'-tris(2-hydroxypropyl)-N-cocoalkyl-1,3-diaminopropane, were chosen to undergo a biocidal evaluation due to their solvating ability for basic copper carbonate against copper-ethanolamine complex as the standard.

The first Comparative Example given below is of the copper/ethanolamine complex, which is the standard compound used to control algae and molds. It shows excellent performance against the brown rot fungus, *G. trabeum*, with a toxic threshold of 0.48 kg/m³, and the white rot fungus, *T. vericolor*, with a toxic threshold of 0.58 kg/m³. However, the compound shows poorer performance against the brown rot fungus, *P. placenta,* with a toxic threshold of 6.85 kg/m$^3$. This last fungus is considered to be tolerant of many simple copper compounds and is representative of a variety of such tolerant fungi.

Pure Ethoduomeen C/13 (Example 2) gave a very poor performance against all three testing fungi. In particular, decay by *G. trabeum* and *T. versicolor* could not be controlled by even 10 kg/m$^3$ and the thresholds had to be determined by extrapolating the weight losses generated at the two highest retentions (thresholds: 18.01 and 21.08 kg/m$^3$ respectively). However, the toxicity of the diamine against *P. placenta* is much greater (toxic threshold: 10.24 kg/m$^3$).

The effectiveness of all four copper-diamine complexes against G. trabeum is very high and consistent with an approximately 0.5 kg/m$^3$ threshold. These four complexes control both attack by *P. placenta* and *T. versicolor*. Moreover, they show an unexpectedly good effect against P. placenta. The formulation of copper-Ethoduomeen C/13 in an 11:1 (wt:wt) ratio (Example 4) was the most effective of those tested, with approximately 0.8 kg/m$^3$ of the formulated chemical being sufficient to control the attack by all three fungi.

A comparison of complexes made with similar ratios of Ethoduomeem C/13 and Propoduomeen C/13 (Examples 5 and 6) showed that the copper/Ethoduomeen complex at a 2:1 wt/wt ratio gave somewhat better control of *P. placenta* (toxic threshold: 0.96 kg/m$^3$) than the similar one made with Propoduomeen C/13 (toxic threshold: 1.83 kg/m$^3$).

The Tests Procedures and Examples which follow set forth certain embodiments of the invention.

TEST PROCEDURES

All biological evaluations were run according to procedures given in the American Wood Preserver's Association Standard E10-91.

The test material consisted of 19 by 19 by 19 mm sapwood blocks prepared from southern yellow pine (Pinus spp.) (for brown-rot fungi) and red alder (*Alnus rubra*) (for white-rot fungus). Due to the similar solution uptakes by southern yellow pine and red alder, the same solution concentration of each chemical was used to treat the blocks of both wood species, at the same time.

A group of 396 southern yellow pine test blocks (6 treatments×2 fungi×6 replicates×5 concentrations, and 10% additional blocks were included), and 198 red alder test blocks (6 treatments×1 fungus×6 replicates×5 concentrations, and 10% additional blocks were included) were oven dried at 103° C. and weighted ($T_1$). The oven dried blocks were then vacuum impregnated with dilutions of the various compounds in either water or toluene. Control blocks were prepared by treating with toluene in the case of Example 2 and 2% ethanolamine in water for the copper-amine complexes.

The 2% ethanolamine solution was chosen for treating the control blocks because ethanolamine had been added into the copper-diamine complexes for filling out the coordination requirement of the complex. Thus, the control blocks of the copper-amine complexes were treated with 2% ethanolamine in water to cancel out any possible biocidal effect caused by ethanolamine. However, such effects are unlikely due to the high water solubility of ethanolamine, since any significant amount of ethanolamine would be leached out during the leach cycle. For the sake of comparison, a set of control blocks treated with water only was also exposed to the testing fungi under the same conditions. The weight losses of the two sets controls did not show any significant difference as observed from the example data in Table 1.

The preservative uptake was determined from the increase in the weight of the blocks following treatment ($T_2-T_1$). The retention of the blocks for each chemical was calculated as follows:

$$\text{Preservative Retention (kg/m}^3\text{)} = \frac{(T_2 - T_1)C}{V} \times 10$$

$T_2T_1$—=grams of treating solution absorbed by the block.

C=grams of preservative in 100 g of treating solution.

V=volume of block in cubic centimeters.

The blocks were then wrapped in plastic bags and stored at 22° C. for about three days, followed by conditioning in the laboratory for two weeks. The blocks were then subjected to a two-week water leach. Each group of blocks (21) was submerged in 400 ml distilled water. The leaching containers were evacuated for 30 min, after which the vacuum was released and the blocks kept submerged during saturation by the distilled water. After one week of static leaching, the leach water was replaced by fresh distilled water. The blocks were then removed and conditioned in the laboratory for two weeks prior to sterilization.

Soil jars (500 ml) containing 250 ml soil were steam sterilized. For *Postia placenta* and *Gloeophyllum trabeum*, the feeder strips were ponderosa pine sapwood, while for *Trametes versicolor* birch sapwood was used. The jars were inoculated with one of the three fungi. The inoculum sections of fungi were cut from the leading edge of the fungal mycelium in petri dish cultures and placed on the soil in contact with the edge of the feeder strip. The jars were sealed with a screw-type metal lid, in which a 5 mm hold had been drilled. The hole was sealed with Gelman GA-82µ Metricel filter, to permit aeration. The jars were incubated at 25° C. for three weeks (until the feeder strips were covered by mycelium).

The blocks, sterilized by exposure to 2.5 Mrad of gamma irradiation, were placed in the previously prepared soil jars (two to a jar) with a cross-sectional face in contact with the feeder strip. The closed soil jars were incubated at 25° C. for twelve weeks.

At the end of the incubation period the blocks were removed from the soil jars and mycelium and soil adhering to the surface carefully brushed away. The weights ($T_3$) of the blocks were recorded, before the blocks were oven dried at 103° C. overnight and weighed again ($T_4$). The weight loss caused by the fungal decay was calculated from the final weight ($T_4$) and the original oven dried weight ($T_1$):

$$\text{Weight loss (\%)} = \frac{T_1 - T_4}{T_1} \times 100\%$$

The moisture content of the blocks after the test was determined by the weight after incubation ($T_3$) and the weight after final oven dry ($T_4$):

$$\text{Moisture content (\%)} = \frac{T_3 - T_4}{T_4} \times 100\%$$

The toxic limits were determined as the highest preservative retention which permitted a mean weight loss in excess of two percent and the lowest retention which produced a mean weight loss of less than two percent. The toxic threshold was determined for each test as the chemical retention at which the weight loss is two percent. For those tests which didn't produce a two percent weight loss within the range of the concentration used, the toxic threshold was obtained by extrapolating the highest two retentions to the point of two percent weight loss.

TABLE 1

| Example # | Formulation* | Toxic Threshold (and Toxic Limits) (kg/m$^3$) | | |
|---|---|---|---|---|
| | | G. trabeum | P. placenta | T. versicolor |
| 1 | Copper/ethanolamine Standard example | 0.48 (0–0.48) | 6.85 (2.11–10.74) | 0.58 (0.51–1.11) |
| 2 | Ethoduomeen C/13 only Control example | 18.01 (>10.69) | 10.24 (2.21–10.69) | 21.08 (>11.39) |
| 3 | Copper/Ethoduomeen C/13 1:5 wt/wt ratio | 0.50 (0–0.52) | 0.67 (0.52–1.05) | 1.45 (1.13–2.26) |
| 4 | Copper/Ethoduomeen C/13 1:1 wt/wt ratio | 0.51 (0–0.53) | 0.52 (0–0.53) | 0.77 (0.53–1.11) |
| 5 | Copper/Ethoduomeen C/13 2:1 wt/wt ratio | 0.48 (0–0.5) | 0.96 (0.5–1.02) | 0.89 (0.54–1.06) |
| 6 | Copper/Propoduomeen C/13 2:1 wt/wt ratio | 0.50 (0–0.52) | 1.83 (1.02–2.09) | 0.61 (0.54–1.09) |

*Ratios are expressed as copper (as CuO) to diamine.

COMPARATIVE EXAMPLE 1

(not according to the invention)

The following concentrate was prepared by mixing the following together until all solids dissolved and a dark blue solution resulted: 9.0% of basic copper carbonate; 18.9% of ethanolamine; and 72.1% of deionized water.

The concentrate was diluted with distilled water to give solutions with 0.07%, 0.14%, 0.28% and 1.4% concentrations of copper. These diluted solutions were used to treat the southern yellow pine and red alder blocks. The blocks were exposed to the three fungi as described above. The toxic threshold and toxic limit values from these tests are presented in Table 1.

COMPARATIVE EXAMPLE 2

(not according to the invention)

Ethoduomeen C/13 was diluted with toluene to give solutions with 0.1%, 0.2%, 0.4% and 2.0% concentrations of the compound. These diluted solutions were used to treat the southern yellow pine and red alder blocks. The blocks were exposed to the three fungi as described above. The toxic threshold and toxic limit values from these tests are presented in Table 1.

EXAMPLE 3

A concentrate was prepared by mixing the following together until all solids dissolved and a dark blue solution resulted: 9.0% of basic copper carbonate; 32.0% of Ethoduomeen C/13; 14.0% of ethanolamine; and 45.0% of deionized water.

The concentrate was diluted with distilled water to give solutions with 0.07%, 0.14%, 0.28% and 1.4% concentrations of the copper and fatty diamine. These diluted solutions were used to treat the southern yellow pine and red alder blocks. The blocks were exposed to the three fungi as described above. The toxic threshold and toxic limit values from these tests are presented in Table 1.

EXAMPLE 4

Another concentrate was also prepared by mixing the following together until all solids dissolved and a dark blue solution resulted: 9.0% of basic copper carbonate; 6.4% of Ethoduomeen C/13; 18.0% of ethanolamine; and 66.6% of deionized water.

The concentrate was diluted with distilled water to give solutions with 0.07%, 0.14%, 0.28% and 1.4% concentrations of the copper and fatty diamine. These diluted solutions were used to treat the southern yellow pine and red alder blocks. The blocks were exposed to the three fungi as described above. The toxic threshold and toxic limit values from these tests are presented in Table 1.

EXAMPLE 5

Yet another concentrate was prepared by mixing the following together until all solids dissolved and a dark blue solution resulted: 9.0% of basic copper carbonate; 3.2% of Ethoduomeen C/13; 18.4% of ethanolamine; and 69.4% of deionized water.

The concentrate was diluted with distilled water to give solutions with 0.07%, 0.14%, 0.28% and 1.4% concentrations of the copper and fatty diamine. These diluted solutions were used to treat the southern yellow pine and red alder blocks. The blocks were exposed to the three fungi as described above. The toxic threshold and toxic limit values from these tests are presented in Table 1.

EXAMPLE 6

Another concentrate was prepared by mixing the following together until all solids dissolved and a dark blue solution resulted: 9.0% of basic copper carbonate; 3.6% of Propoduomeen C/13; 18.4% of ethanolamine; and 69.0% of deionized water.

The concentrate was diluted with distilled water to give solutions with 0.07%, 0.14%, 0.28% and 1.4% concentrations of the copper and fatty diamine. These diluted solutions were used to treat the southern yellow pine and red alder blocks. The blocks were exposed to the three fungi as described above. The toxic threshold and toxic limit values from these tests are presented in Table 1.

The foregoing Examples are presented for illustrative purposes only and for that reason should not be con-

I claim:

1. A formulation for the preservation of wood which comprises a solvent having dissolved therein a complex formed by reaction of a compound containing a copper cation and an alkoxylated diamine.

2. A formulation as claimed in claim 1 wherein the liquid solvent consists essentially of water.

3. A formulation as claimed in claim 1 wherein the alkoxylated diamine is selected from the group consisting of an ethoxylated diamine and a propoxylated diamine.

4. A formulation as claimed in claim 1 wherein the diamine comprises at least one fatty alkyl group.

5. A formulation as claimed in claim 2 wherein the diamine comprises at least one fatty alkyl group.

6. A formulation as claimed in claim 3 wherein the diamine comprises at least one fatty alkyl group.

7. A formulation as claimed in claim 1 wherein the weight ratio of copper cation, expressed as CuO, to alkoxylated diamine is from about 1:30 to about 5:1.

8. A formulation as claimed in claim 7 wherein the alkoxylated diamine is selected from the group consisting of an ethoxylated diamine and a propoxylated diamine.

9. A formulation as claimed in claim 8 wherein the diamine comprises at least one fatty alkyl group.

10. A formulation as claimed in claim 1 which further comprises a small coordinating amine to fill out the coordination needs of the copper.

11. A formulation as claimed in claim 3 which further comprises a small coordinating amine to fill out the coordination needs of the copper.

12. A formulation as claimed in claim 7 which further comprises a small coordinating amine to fill out the coordination needs of the copper.

13. A formulation as claimed in claim 8 which further comprises a small coordinating amine to fill out the coordination needs of the copper.

* * * * *